(12) United States Patent
Cousins

(10) Patent No.: US 9,005,148 B2
(45) Date of Patent: Apr. 14, 2015

(54) ORTHOTIC HEAD AND NECK SUPPORT

(75) Inventor: Steven John Cousins, Shaftesbury (GB)

(73) Assignee: Matrix Seating Limited, Shaftesbury Dorset (GB)

( * ) Notice: Subject to any disclaimer, the term of this patent is extended or adjusted under 35 U.S.C. 154(b) by 319 days.

(21) Appl. No.: 13/392,071

(22) PCT Filed: Aug. 17, 2010

(86) PCT No.: PCT/GB2010/051358
§ 371 (c)(1),
(2), (4) Date: Feb. 23, 2012

(87) PCT Pub. No.: WO2011/023984
PCT Pub. Date: Mar. 3, 2011

(65) Prior Publication Data
US 2012/0174930 A1     Jul. 12, 2012

(30) Foreign Application Priority Data

Aug. 26, 2009   (GB) .................................. 0914865.1

(51) Int. Cl.
*A61F 5/00*     (2006.01)
*A61F 5/055*    (2006.01)

(52) U.S. Cl.
CPC ..................... *A61F 5/055* (2013.01)

(58) Field of Classification Search
USPC ........ 128/846, 869, 870, 874; 602/17–20, 32, 602/36, 37; 2/102, 113, 126, 462, 467; 606/286, 289
See application file for complete search history.

(56) References Cited

U.S. PATENT DOCUMENTS

| | | | | |
|---|---|---|---|---|
| 2,223,276 A | * | 11/1940 | Ward | 602/18 |
| 4,325,363 A | | 4/1982 | Berkeley | |
| 4,582,051 A | * | 4/1986 | Greene et al. | 602/18 |
| 5,060,637 A | | 10/1991 | Schmid et al. | |
| 5,433,696 A | | 7/1995 | Osti | |
| 6,315,746 B1 | * | 11/2001 | Garth et al. | 602/18 |
| 6,726,643 B1 | * | 4/2004 | Martin | 602/18 |

FOREIGN PATENT DOCUMENTS

| | | |
|---|---|---|
| EP | 0 655 232 A1 | 5/1995 |
| EP | 1 563 813 A2 | 8/2005 |
| GB | 2 126 485 A | 3/1984 |
| JP | 08-066416 A | 3/1996 |
| WO | WO 99/43275 | 9/1999 |

* cited by examiner

*Primary Examiner* — Michael A. Brown
(74) *Attorney, Agent, or Firm* — Blakely Sokoloff Taylor & Zafman

(57) ABSTRACT

A kit of parts for forming an orthotic head support. The kit includes at least one frame having a plurality of arms extending from a central region. Examples of such frames are W-frames, Y-frames and H-frames. The kit further includes at least one extension connectable to a frame. Such extension members include straight extensions, L-shaped extensions, and extension with two elements at an acute angle to one another. The kit has elements for attaching the extensions to the frames. The frames and extensions may have lines of reduced stiffness formed therein about which they are preferentially bendable to conform the support to the shape of a wearer's head and/or neck. The kit further includes padding members connected, or connectable, to the frames and/or extensions on the surfaces thereof which in use are to be adjacent the wearer.

20 Claims, 14 Drawing Sheets

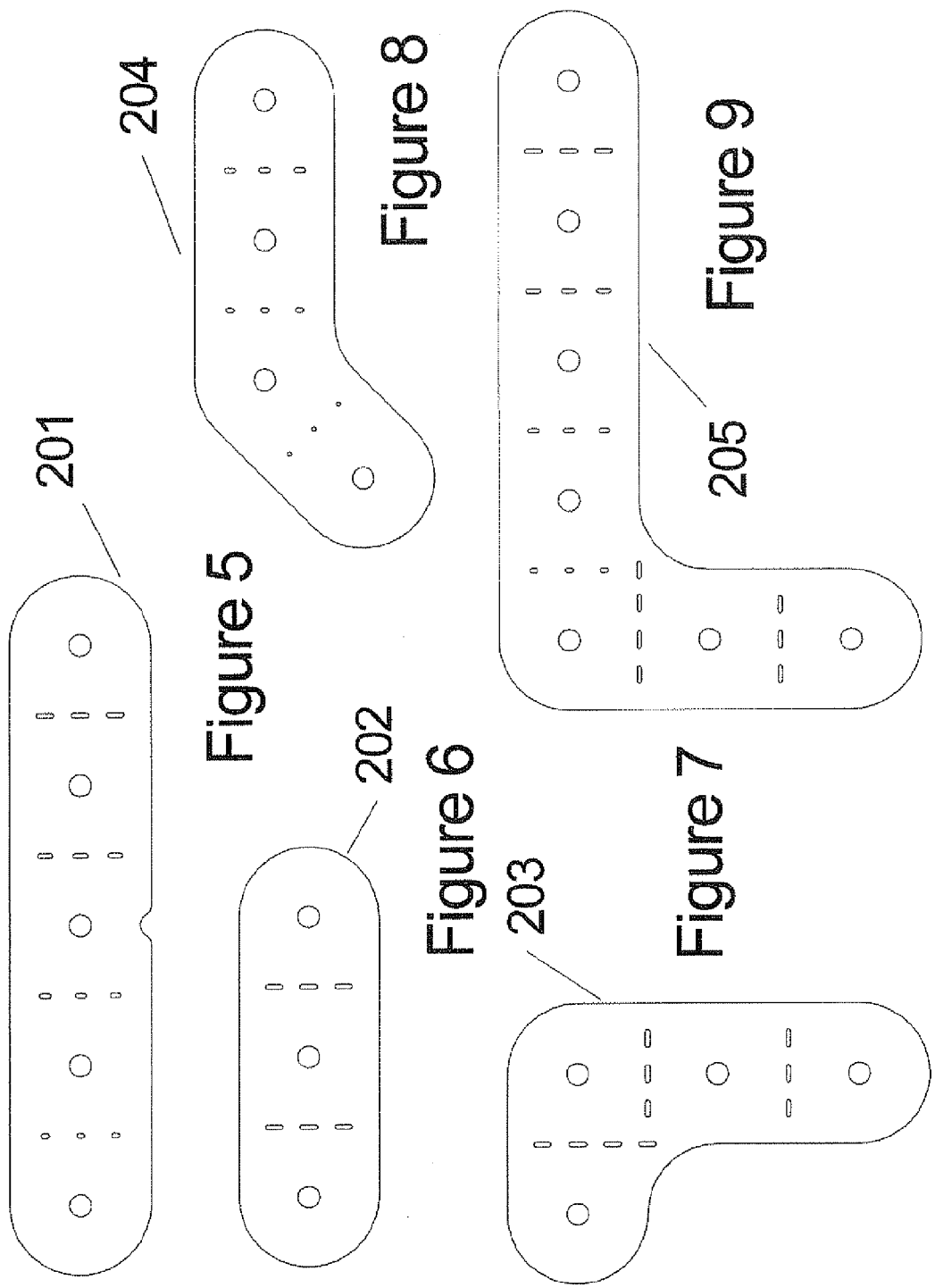

ORTHOTIC HEAD AND NECK SUPPORT

This is a non-provisional application claiming the benefit of International Application Number PCT/GB2010/051358 filed Aug. 17, 2010.

This invention relates to an orthotic head and neck support.

Head and neck support for people with a permanent or temporary disability can be complex. The individual may have varying degrees of muscle strength, from total paralysis to high tone and uncontrolled muscle spasticity and tremor. Many skeletal parts of the head are subcutaneous (bone just under the skin) and are at risk of pressure injury even when a low pressure is applied for a short period of time. Ears are particularly vulnerable with large head rests and individuals who cannot reposition their heads. Also the head is very mobile, with many possible combinations of rotational and translational movements, which can make positioning difficult.

Superimposed on these complexities are specific pathological combinations. For example, with head injury there can be perceptual/cognitive problems (pulling and positioning the head in awkward positions), removal of cranial bones and non-anatomical shapes as a result of trauma. In other conditions problems arise, for example, from abnormal bone growth, fixed deformities as a result of abnormal muscle pull and physiological imbalances (swelling).

A range of head and neck support shapes and padding is therefore required just to allow the head to be simply in a resting position. If prevention of deformity, corrective positioning and pressure injury risk management are some of the goals then a custom made orthosis (a device applied to the outside of the body to support, aid, and align the body) is required. Custom made, or bespoke, head orthoses are time consuming to fabricate and therefore costly. In most cases they are not even contemplated as a treatment option, since as a result of the problems listed above they would be deemed too difficult, or even impossible, to offer successfully.

The present invention provides a head and neck support system which is modular, and so makes it possible to accommodate the wide range of variables described above. The system is made of a number of components, namely one or more type of frame (in the illustrated form there are three types of frame), and at least one type of extension (in the illustrated form there are five types of extension), which can be connected to the frames in various combinations. Additionally a mass producible modular padding system is described that allows the various modular components to be suitably padded, for safe interfacing to the head and neck.

Thus, according to the invention there is provided a kit of parts for forming an orthotic head and neck support, comprising at least one frame having a plurality of arms extending from a central region, at least one extension connectable to a frame, and means for attaching the extension to the frame, the frame or extension, as the case may be, being bendable to conform the support to the shape of a wearer's head and/or neck, the kit further comprising padding members connected, or connectable, to the frame and/or extension on the surface thereof which in use is to be adjacent the wearer. At least one frame in a kit, optionally all frames in a kit, and/or at least one extension in a kit, optionally all extensions in a kit, may have at least one line of reduced stiffness formed therein, about which the frame or extension is preferentially bendable.

The invention is described below with reference to an illustrated embodiment. In the accompanying drawings:

FIGS. 1A to 1F, taken collectively, show a map of numerous head and neck supports built using the components illustrated therein, and shown in more detail in subsequent figures;

FIGS. 5 to 9 show five modules, herein referred to as extensions, which can be added to the frames to produce head and neck supports;

Figure 1A:
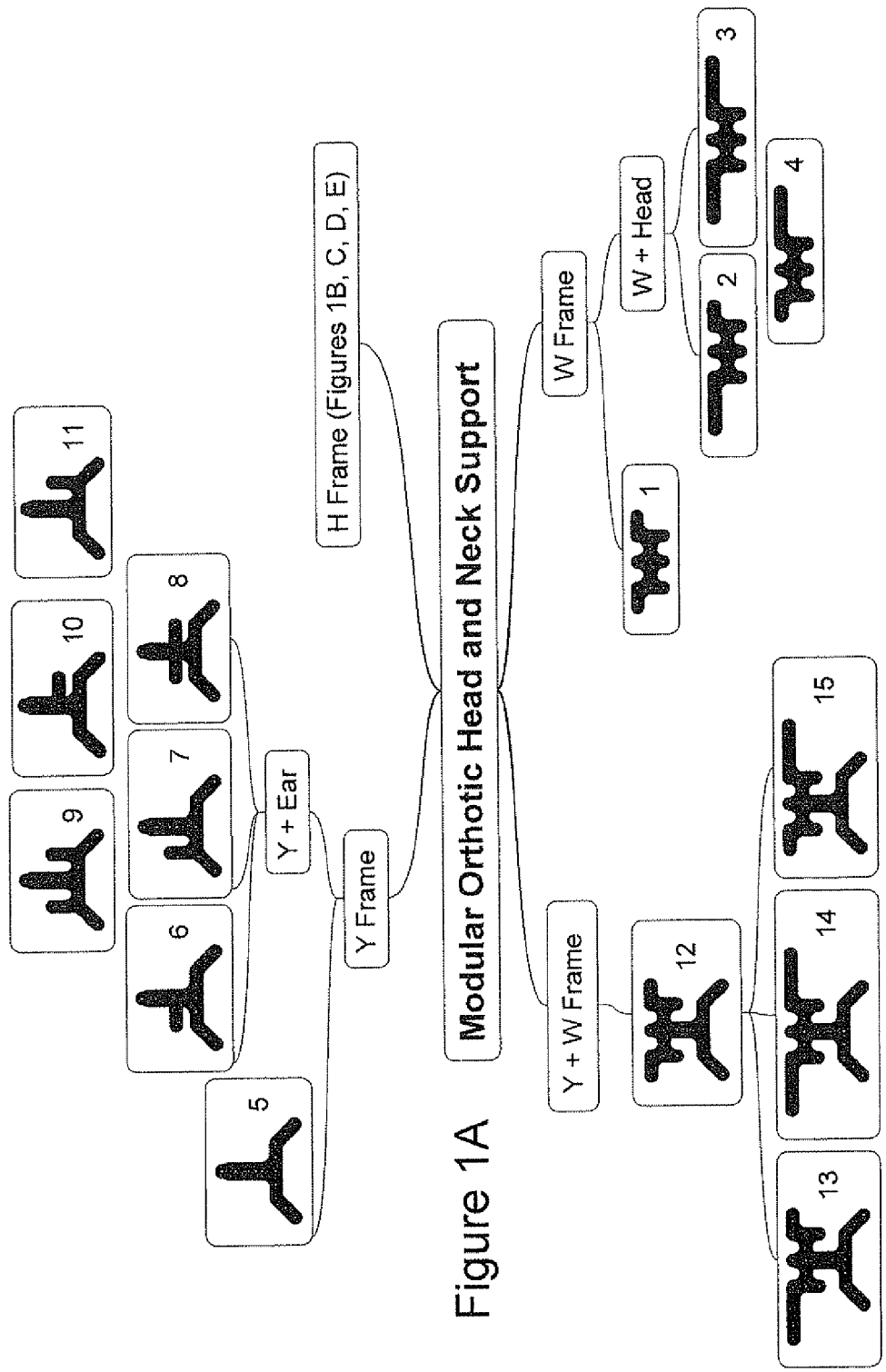
Figure 1B:
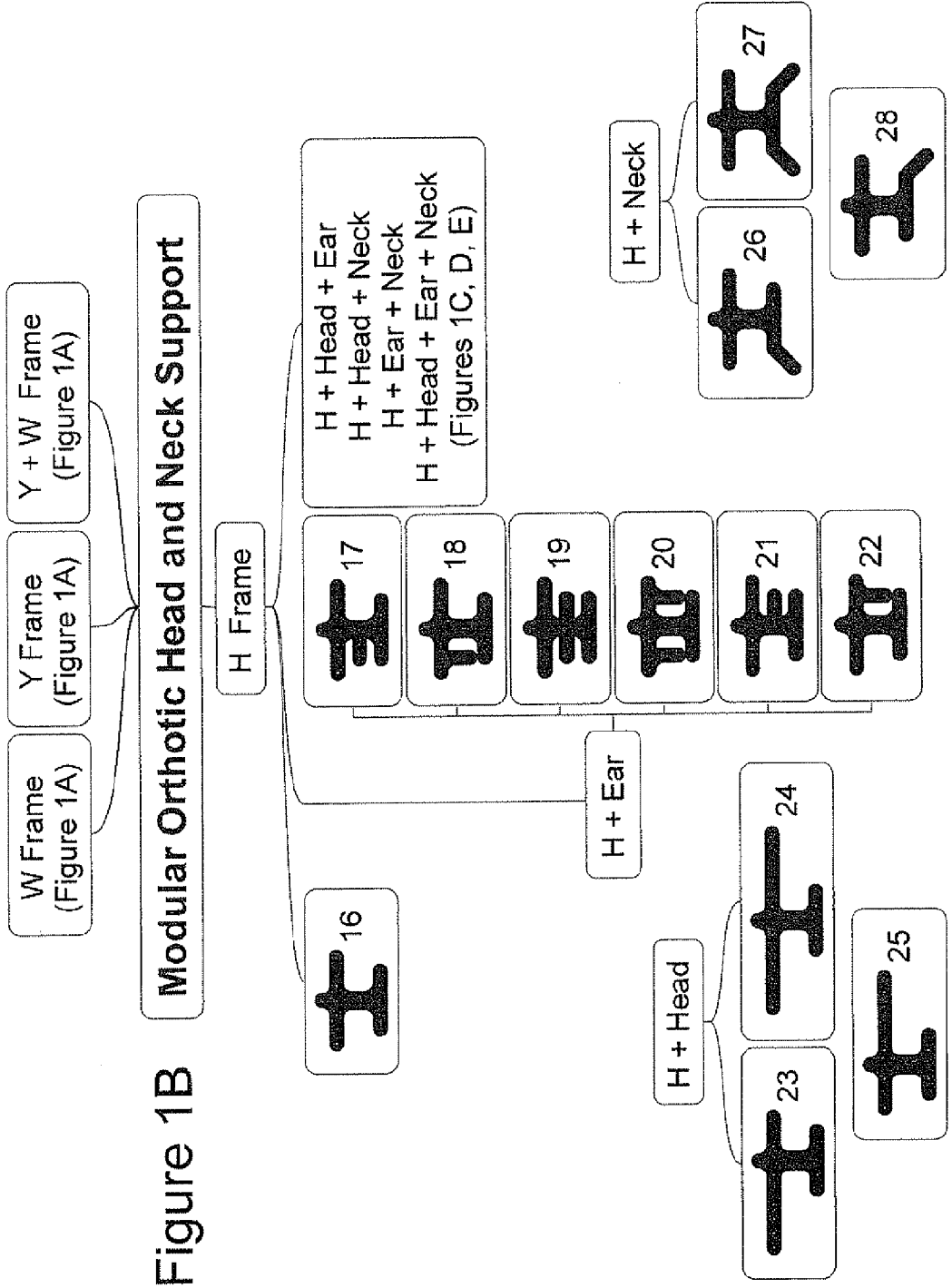
Figure 1C:
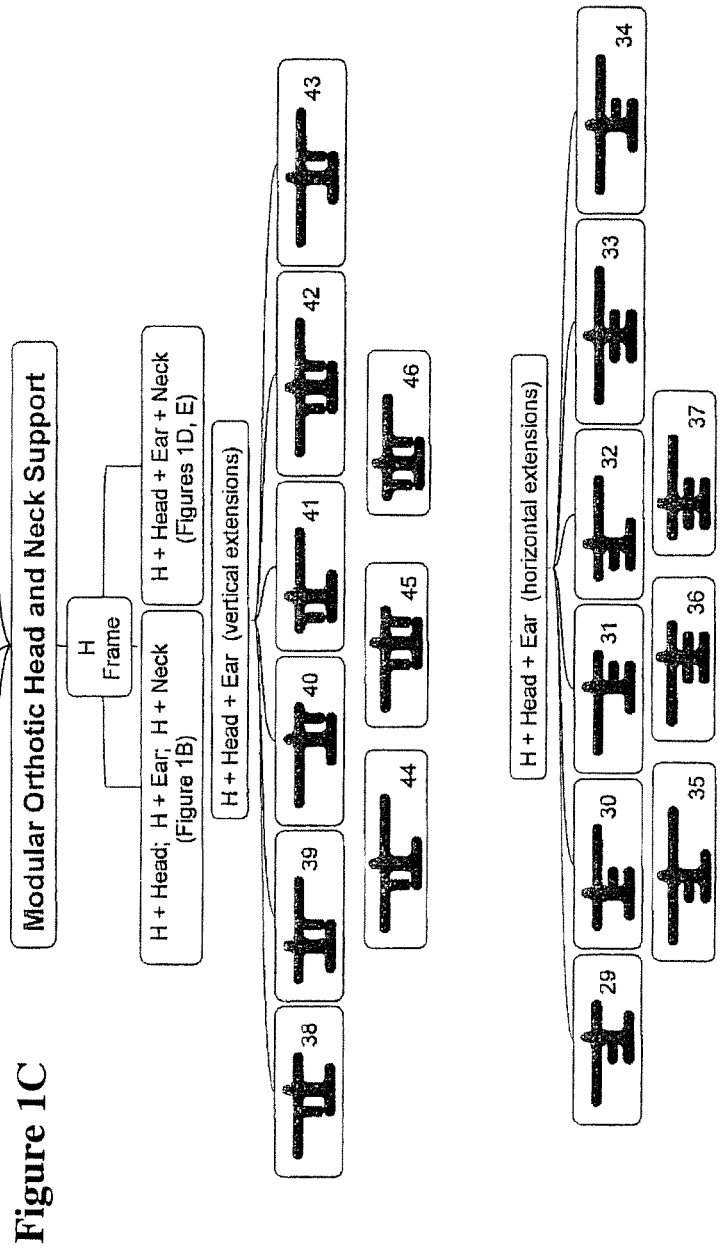
Figure 1D:
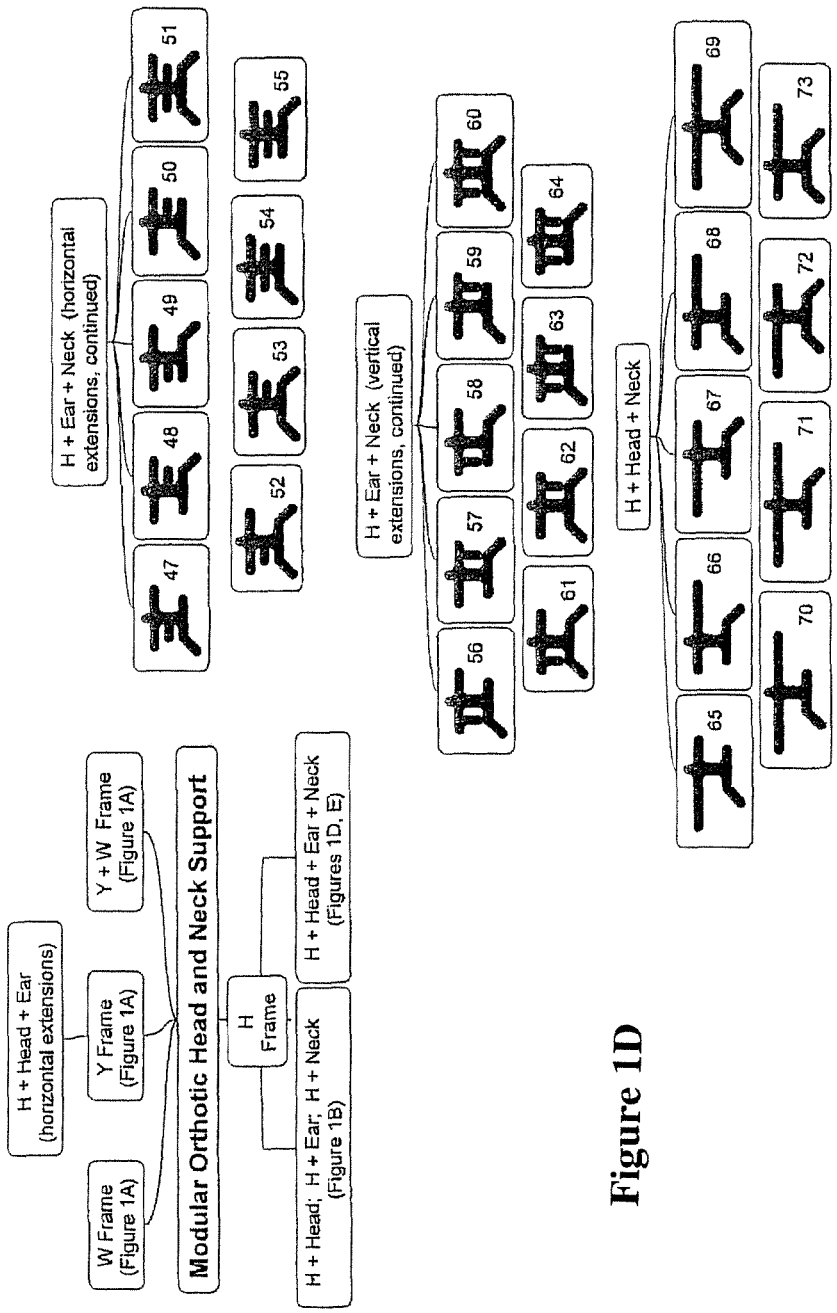
Figure 1E:
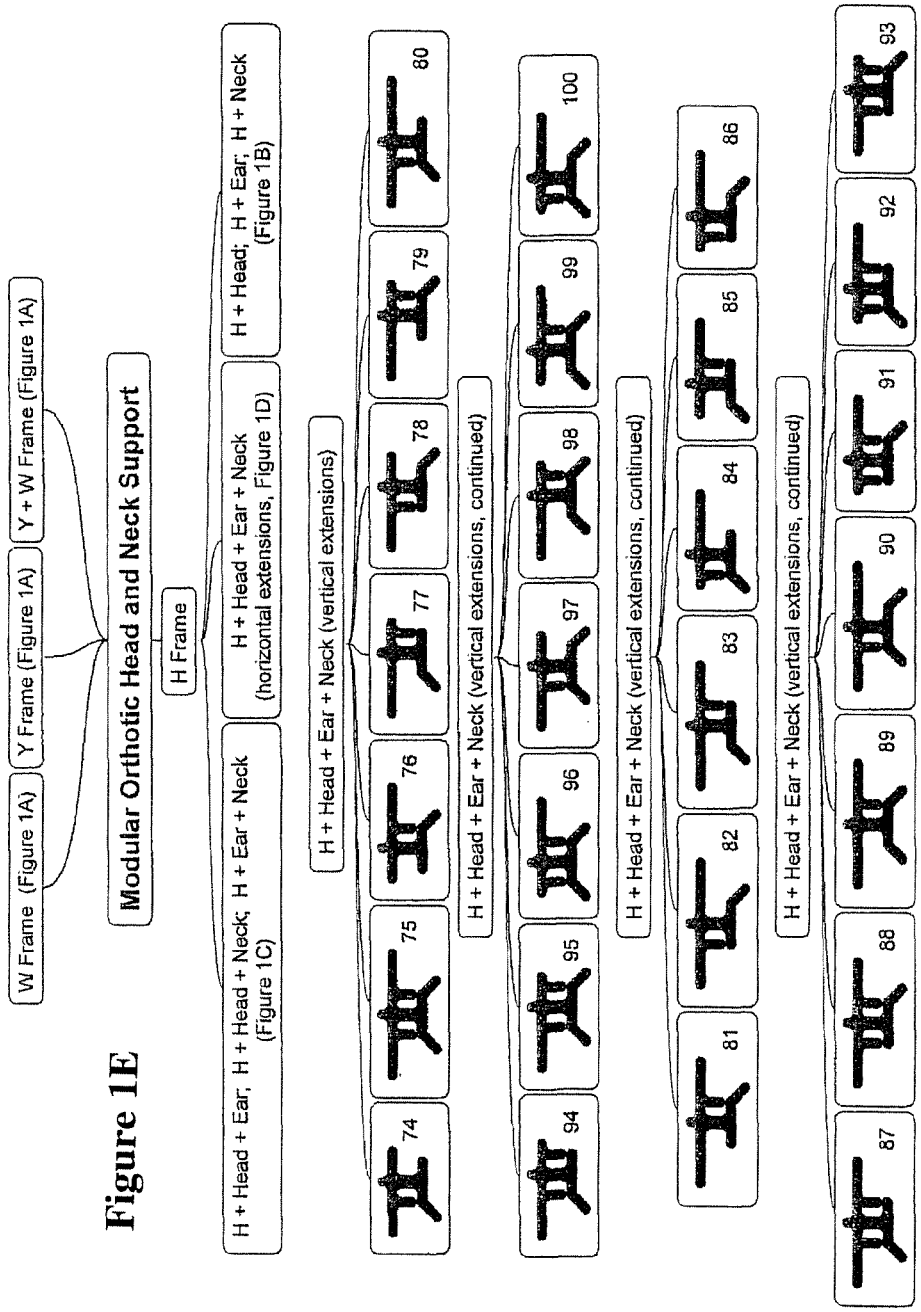
Figure 1F:
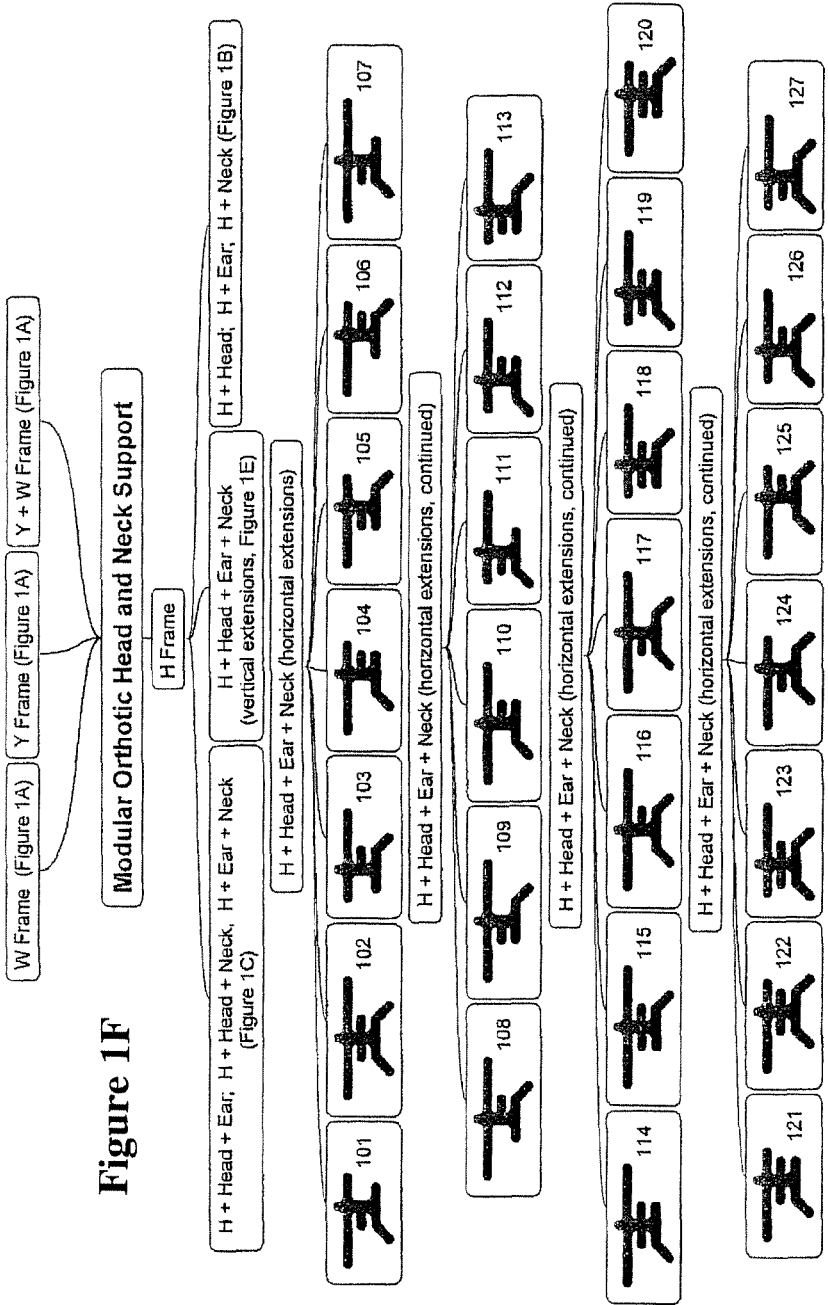

A description will be given first of the three frames shown in FIGS. 2 to 4. The words "vertical", horizontal" and other words denoting orientation, as used in this description and in the claims below, are to be understood as referring to the orientations as they appear in the drawings. In use of the components they would normally be at least generally orientated as illustrated, but not necessarily so. The term "unit" denotes an arbitrary unit of length which is the distance between adjacent connection holes (referred to in more detail below) and also the distance between adjacent lines of reduced stiffness (also referred to below), where present. In practice, for use with adults a "unit" is preferably 30 to 45 mm, more preferably 35 to 40 mm, and most preferably about 38 mm. For use with children a unit is preferably 27 to 37 mm, more preferably 30 to 35 mm, most preferably about 32 mm.

Figure 2:
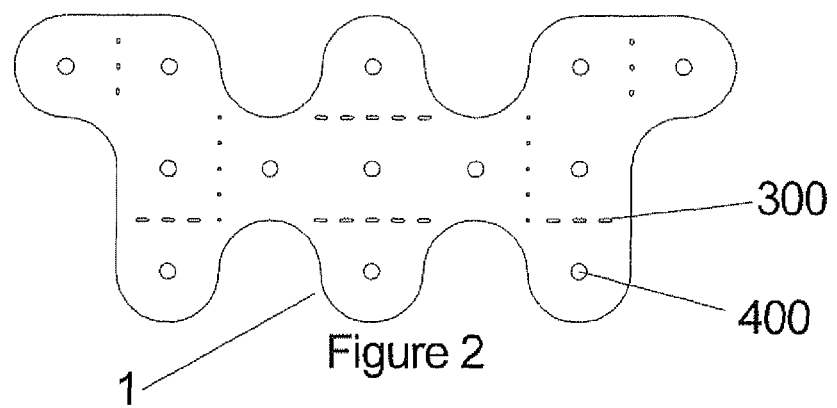
FIGS. 2, 3 and 4 show, in plan view, three basic frames, namely a W frame, an inverted Y frame (referred to herein simply as a Y frame) and a sideways H frame (referred to herein simply as an H frame)

The W-frame 1 of FIG. 2 can be regarded as being made up of three parallel vertical elements, each three units in length, with each adjacent pair being interconnected at their middle regions so as to define a horizontal element five units long, and with a one-unit element extending outwardly from the upper end of each of the outermost vertical elements. Lines of apertures 300, in the form of slots or circular apertures are provided in the W-frame at various locations, to provide regions of reduced stiffness. These permit the W-frame to be bent along predetermined lines to form a three-dimensional structure. The bending of frames is described in more detail below with reference to FIG. 14 which shows the bending of the Y-frame.

Figure 3:
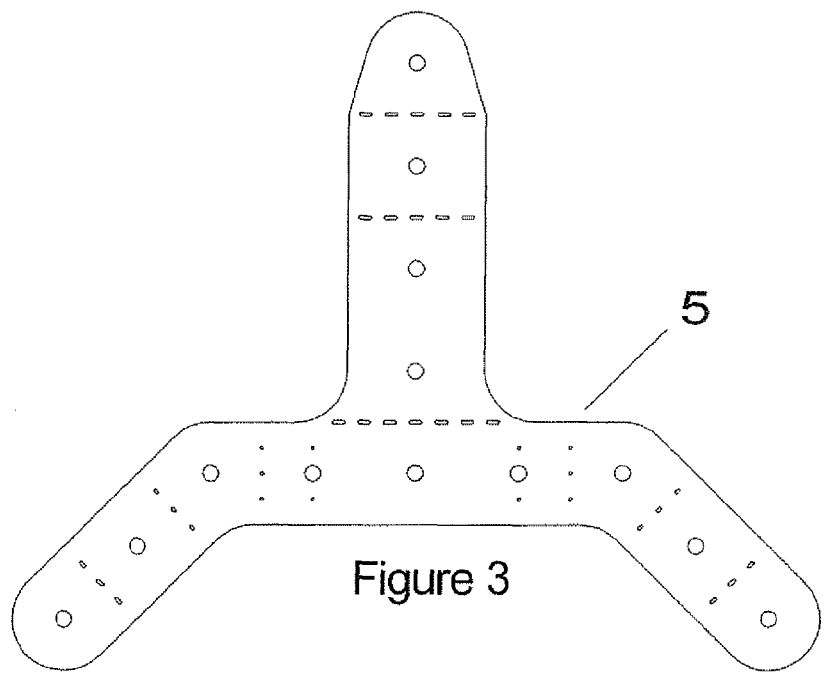

The Y-frame 5 shown in FIG. 3 can be regarded as being made up of a vertical element four units in length, with a horizontal element five units in length at the bottom of the vertical element, and with two elements, each three units in length, extending from the outer end of a respective one of the outer ends of the horizontal element at an acute angle with respect to it, which is preferably 45°.

Figure 4:
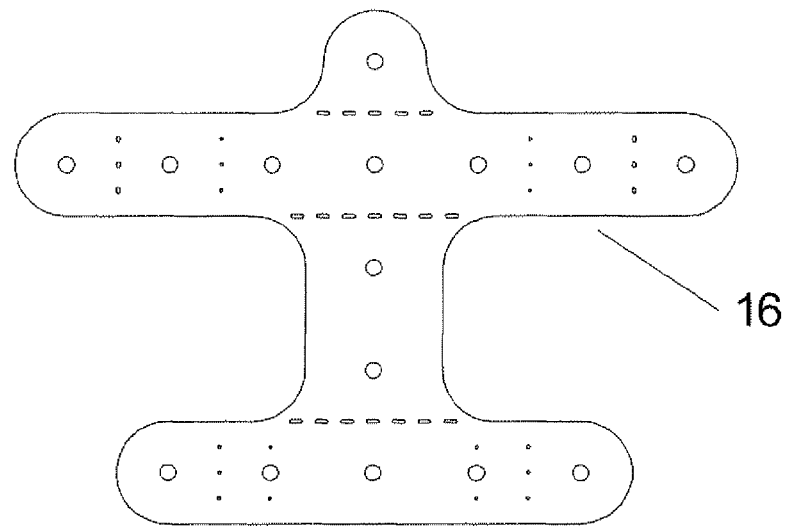
Figure 10:
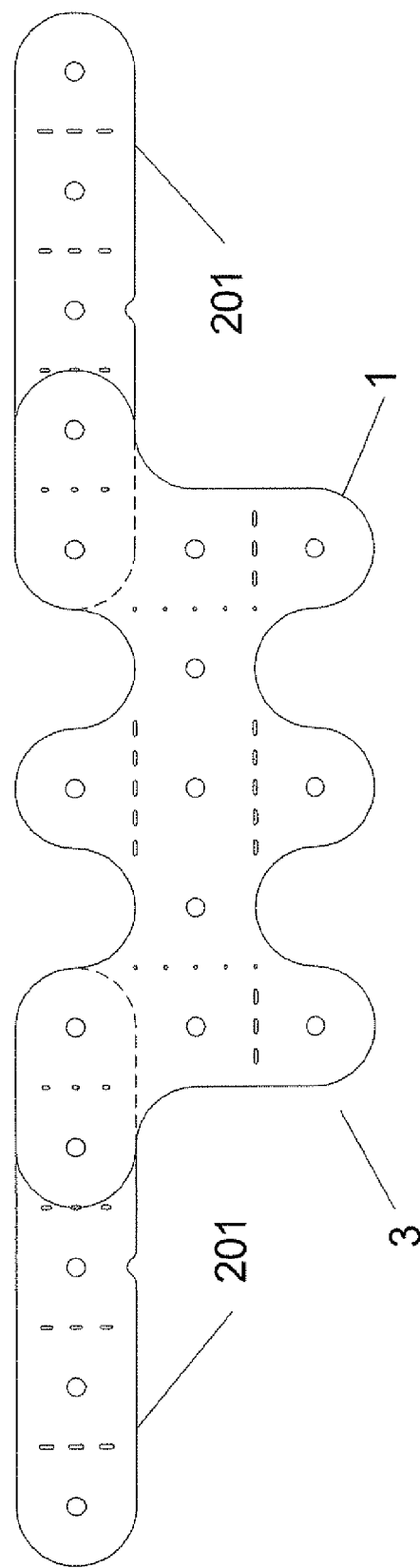
FIGS. 10 to 13 show, by way of example, three of the supports included in the map of FIG. 1.
Figure 11:
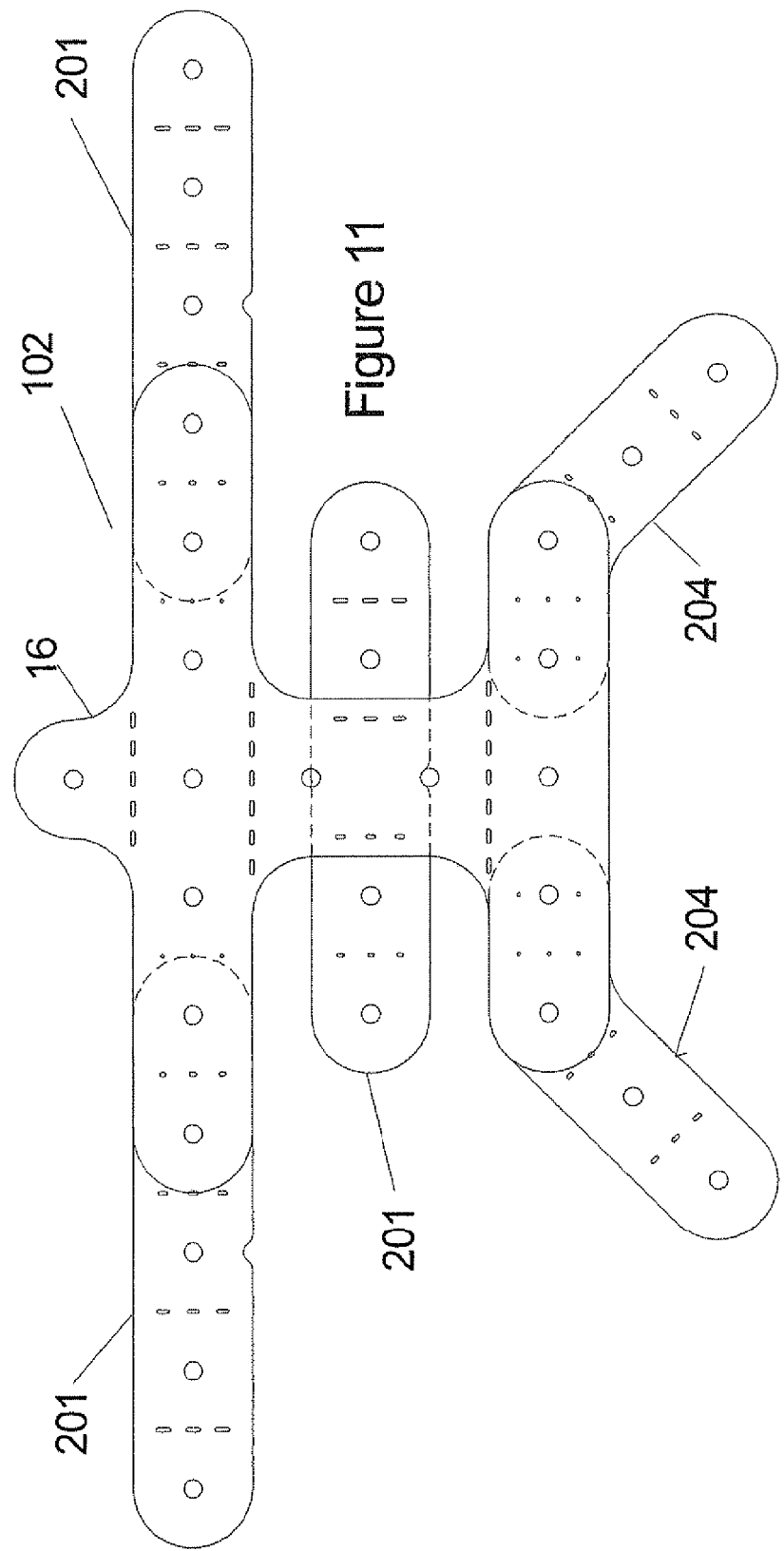
Figure 12:
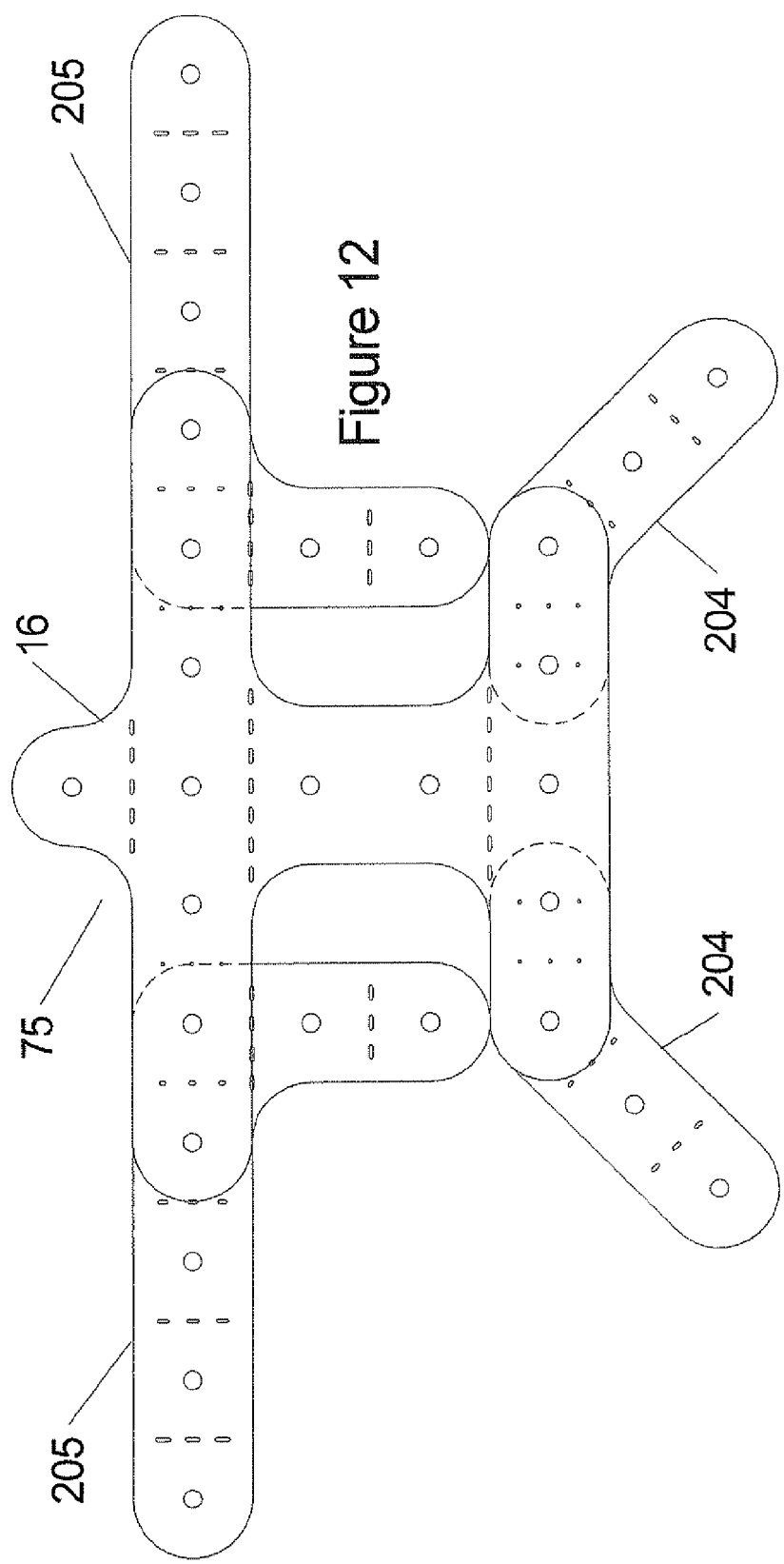
Figure 13:
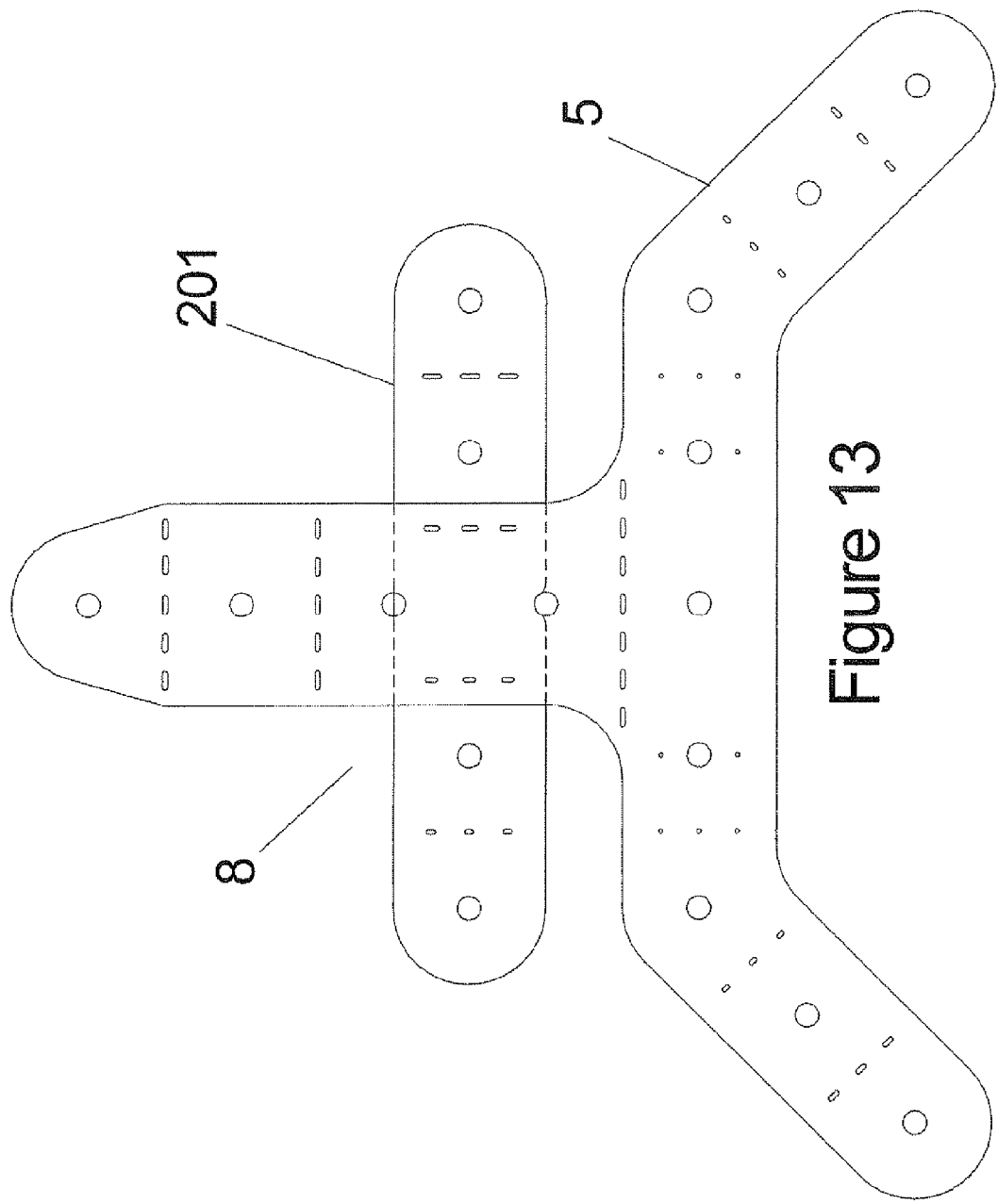

The H-frame 16 shown in FIG. 4 can be regarded as being made up of two horizontal elements, the upper one of which is seven units in length and the lower of which is five units in length, interconnected intermediate their ends, and preferably midway between their ends, by a vertical element two units in length, and with a further vertical element one unit in length extending upwardly from the upper horizontal element.

In use on a wearer, one or more of the above described frames is used in conjunction with one or more of a number of extensions. These are shown in FIGS. 5 to 9, and will now be described.

The extensions 201, 202 shown in FIGS. 5 and 6 are both straight extensions, and they are five and three units long, respectively. The extensions 203, 205 shown in FIGS. 7 and 9 are L-shaped. Each is made up of a vertical element three units long. The extension of FIG. 7 has a horizontal element two units long and the extension of FIG. 9 has a horizontal element five units long. The angled extension 204 of FIG. 8 is made up of a horizontal element three units long, with an element two units long extending from one end thereof at an acute angle thereto, preferably 45°.

Numerous structures, to provide the skeleton of head and neck support structures can be formed by different frame and extension combinations. A table giving 127 such combinations is set out below.

TABLE

| | W | Y | H | 3 | 2L | 3Angle | 5 | 5L | Strap/Anterior Support |
|---|---|---|---|---|---|---|---|---|---|
| 1 | x | | | | | | | | |
| 2 | x | | | | | | x | | x |
| 3 | x | | | | | | xx | | x |
| 4 | x | | | | | | x | | x |
| 5 | | x | | | | | | | |
| 6 | | x | | x | | | | | |
| 7 | | x | | | x | | | | |
| 8 | | x | | | | | x | | |
| 9 | | x | | | xx | | | | |
| 10 | | x | | x | | | | | |
| 11 | | x | | | x | | | | |
| 12 | x | x | | | | | | | |
| 13 | x | x | | | | | x | | x |
| 14 | x | x | | | | | xx | | x |
| 15 | x | x | | | | | x | | x |
| 16 | | | x | | | | | | |
| 17 | | x | x | | | | | | |
| 18 | | | x | | x | | | | |
| 19 | | | x | | | | x | | |
| 20 | | | x | | xx | | | | |
| 21 | | x | x | | | | | | |
| 22 | | | x | x | | | | | |
| 23 | | | x | | | | x | | x |
| 24 | | | x | | | | xx | | x |
| 25 | | | x | | | | x | | x |
| 26 | | | x | | | x | | | |
| 27 | | | x | | | xx | | | |
| 28 | | | x | | | x | | | |
| 29 | | | x | x | | | x | | x |
| 30 | | | x | x | | | x | | x |
| 31 | | | x | x | | | x | | x |
| 32 | | | x | x | | | x | | x |
| 33 | | | x | | | | xxx | | x |
| 34 | | | x | x | | | xx | | x |
| 35 | | | x | x | | | xx | | x |
| 36 | | | x | | | | xx | | x |
| 37 | | | x | | | | xx | | x |
| 38 | | | x | | | | | x | x |
| 39 | | | x | | | | | x | |
| 40 | | | x | | x | | x | | x |
| 41 | | | x | | x | | x | | x |
| 42 | | | x | | | | xx | | x |
| 43 | | | x | | | | x | x | x |
| 44 | | | x | | | | x | x | x |
| 45 | | | x | x | | | | x | x |
| 46 | | | x | x | | | | x | x |
| 47 | | | x | x | x | x | | | |
| 48 | | x | x | x | x | | | | |
| 49 | | x | x | x | x | | | | |
| 50 | | x | x | x | | | | | |
| 51 | | | x | | | xx | x | | |
| 52 | | x | x | | | xx | | | |
| 53 | | x | x | | | xx | | | |
| 54 | | | x | | | x | x | | |
| 55 | | | x | | | x | x | | |
| 56 | | | x | x | | x | | | |
| 57 | | | x | x | | x | | | |
| 58 | | | x | x | | x | | | |
| 59 | | | x | x | | x | | | |
| 60 | | | x | | xx | xx | | | |
| 61 | | | x | x | | xx | | | |
| 62 | | | x | x | | xx | | | |
| 63 | | | x | | xx | x | | | |
| 64 | | | x | xx | x | | | | |
| 65 | | | x | | | x | x | | x |
| 66 | | | x | | | x | x | | x |
| 67 | | | x | | | x | x | | |
| 68 | | x | | | | x | x | | x |
| 69 | | x | | | | xx | xx | | x |
| 70 | | x | | | | x | xx | | x |
| 71 | | x | | | | x | xx | | x |
| 72 | | x | | | | xx | x | | x |
| 73 | | x | | | | xx | x | | x |
| 74 | | x | | | | x | | x | x |
| 75 | | x | | | | xx | | xx | x |
| 76 | | x | | | | x | | x | x |
| 77 | | x | | x | | x | | | x |
| 78 | | x | | | | x | | x | x |
| 79 | | x | | x | | x | x | | x |
| 80 | | x | | | | x | x | x | x |
| 81 | | x | | | | x | x | x | x |
| 82 | | x | | | | x | x | x | x |
| 83 | | x | | | | x | x | x | x |
| 84 | | x | | x | | x | x | | x |
| 85 | | x | | | | x | | x | x |
| 86 | | x | | x | | x | x | | x |
| 87 | | x | | | | x | | xx | x |
| 88 | | x | | | | x | | xx | x |
| 89 | | x | | | | xx | x | x | x |
| 90 | | x | | | | xx | x | x | x |
| 91 | | x | | x | | x | | x | x |
| 92 | | x | | x | | x | | x | x |
| 93 | | x | | x | | x | | x | x |
| 94 | | x | | x | | x | | x | x |
| 95 | | x | | x | | xx | | x | x |
| 96 | | x | | x | | xx | | x | x |
| 97 | | x | | | | xx | | x | x |
| 98 | | x | | x | | xx | x | | x |
| 99 | | x | | | | xx | | x | x |
| 100 | | x | | x | | xx | x | | x |
| 101 | x | x | | | | x | x | | x |
| 102 | | x | | | | xx | xxx | | x |
| 103 | x | x | | | | x | x | | x |
| 104 | x | x | | | | x | x | | x |
| 105 | x | x | | | | x | x | | x |
| 106 | x | x | | | | x | x | | x |
| 107 | x | x | | | | x | xx | | x |
| 108 | x | x | | | | x | xx | | x |
| 109 | x | x | | | | x | xx | | x |
| 110 | x | x | | | | x | xx | | x |
| 111 | x | x | | | | x | x | | x |
| 112 | x | x | | | | x | x | | x |
| 113 | x | x | | | | x | x | | x |
| 114 | | x | | | | x | xxx | | x |
| 115 | | x | | | | x | xxx | | x |
| 116 | x | x | | | | xx | xx | | x |
| 117 | x | x | | | | xx | xx | | x |
| 118 | | x | | | | x | | xx | x |
| 119 | | x | | | | x | | xx | x |
| 120 | | x | | | | x | | xx | x |
| 121 | | x | | | | x | | xx | x |
| 122 | | x | | | | xx | xx | | x |
| 123 | | x | | | | xx | xx | | x |
| 124 | x | x | | | | xx | x | | x |
| 125 | x | x | | | | xx | x | | x |
| 126 | x | x | | | | xx | x | | x |
| 127 | x | x | | | | xx | x | | x |

In the above table, the first three columns, which are headed W, Y and H, denote the use of a W-frame, Y-frame or H-frame. In some cases two frames are used (combinations 12-15, 48, 49, 50, 52, 54, 101, 103-113, 116, 117 and 124-127). In the remaining cases one of the frames is used.

The next five columns show which extensions are used, the headings to the columns representing:

3=three-unit straight extension (FIG. 6)

2L=L-shaped unit with two-unit horizontal element (FIG. 7)

3Angle=angled unit of FIG. 8

5=five-unit straight extension (FIG. 5)

5L=L-shaped unit with five-unit horizontal element (FIG. 9)

As can be seen, in some combinations, two, or even three extensions of a particular sort are required, a fact which is denoted in the table by the presence of two or three symbols in the column referring to that particular extension.

The final column indicates whether it would be desirable to provide a strap or anterior support to go across the wearer's forehead to hold the whole structure in position. Such a strap or anterior support, if provided, would extend from one or both of the lateral ends of the structure and across the forehead. The term "strap" is used herein to refer to an entity which is flexible. The term "anterior support", as used herein, is used to refer to a rigid member. Such a rigid member could in fact be constituted by one of the extensions already described, for example the five-unit extension. The rigid member would need to be readily detachable at one end to allow the wearer's head to be moved into and out of the whole structure, as necessary.

Figure 16:
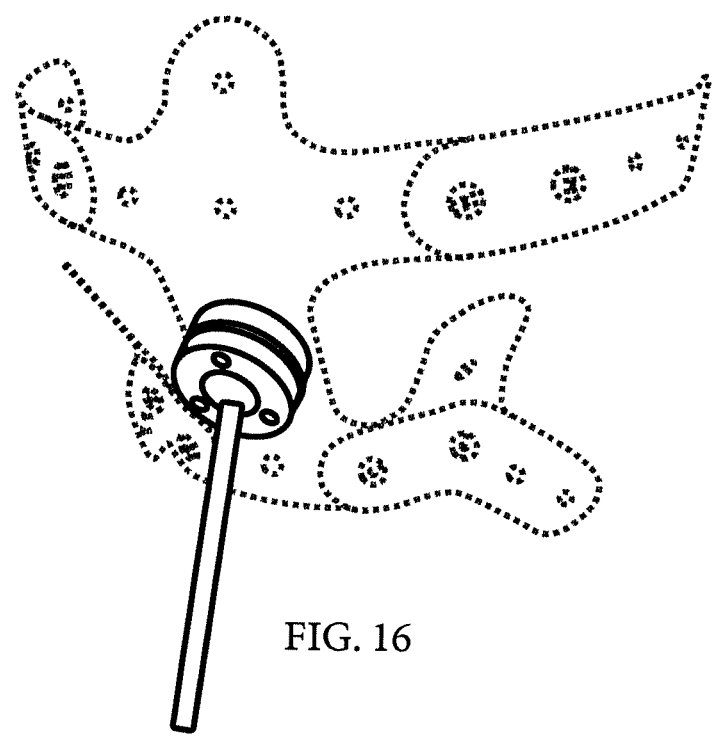
FIG. 16 shows a mounting bracket and a frame in shadow line.

Each frame and extension has a plurality of connection apertures 400 formed therethrough to enable the frame or extension concerned to be attached to another frame or extension. Attachment can be effected by any suitable means, though preferably the attachment is such that the components can be disconnected from one another when the support needs to be changed for a given wearer, or when it is no longer required (so the components can be reused for some other wearer). Preferably attachment is made by connectors of the type known as Chicago screws, or binding screws, which are low profile interscrews. As well as using the holes to attach extensions to a frame, some of the holes are used to attach the skeleton to mounting brackets, which, in turn are attached to the chair, bed or other structure in which the wearer is sitting or lying. One suitable mounting bracket is shown in FIG. 16 which also shows, by way of example only, a specific frame in shadow line to which the bracket may be connected.

FIGS. 10-13 show four of the combinations from the above table, namely those denoted as combinations 3, 102, 75 and 8, respectively. As with all the illustrated combinations, these are put together from the appropriate frames and extensions by overlapping the components to be connected by an amount equal to two units, and then inserting a connector, e.g. a Chicago screw through each of the two pairs of aligned apertures.

As an alternative, however, some of the apertures may be replaced by protrusions of a size which enables it to be received snugly in an aperture in another component. Attachment of one component to another can then be made by aligning an aperture 400 in a first component with an aperture 400 in a second component, and receiving a protrusion on the first component in another aperture 400 in the second component. A screw attachment is them made via the aligned apertures.

Whether by two pairs of aligned apertures, or by one pair of aligned apertures and one combination of protrusion and aperture, the two components are thus held securely together without any possibility of one pivoting with respect to the other. The thickness of the combination is therefore never more than two times the thickness of the material of which the components are made (assuming that all components are of the same thickness as one another. This is desirable from the point of view of reducing the risk of excessive pressures being applied to the wearer's head at any location.

The combinations shown in FIGS. 10-13 are shown in a planar state. However, in order to act as skeletons for head and neck supports they need to be bent out of the planar condition, in accordance with the particular way in which the given wearer's head and neck needs to be supported. This bending can take place either before or after the components are attached to one another. An example of the nature of such bending is given in FIG. 14, which shows the bending of an H-frame. The H-frame is shown, in this example, being bent along six of the bending axes defines by lines of slots.

Figure 15:
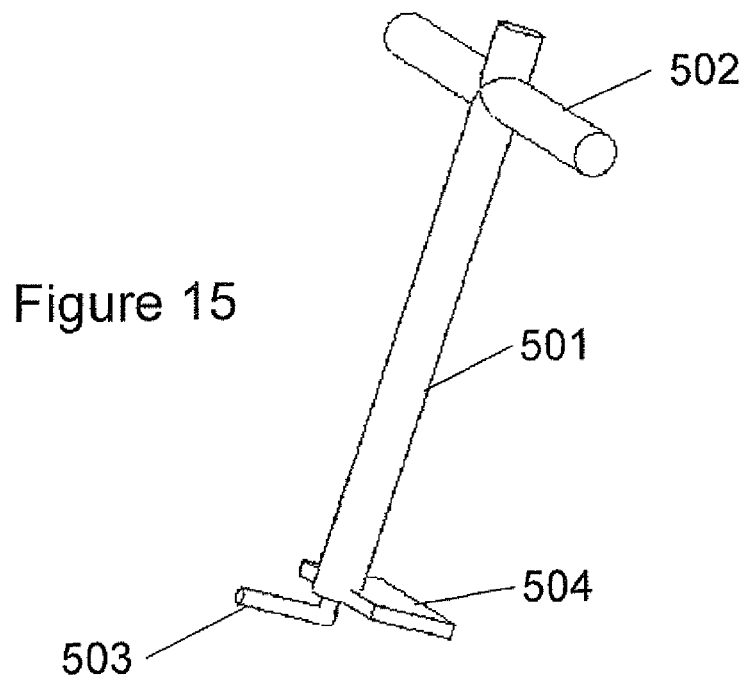
FIG. 15 shows, in perspective, a tool for use in effecting that bending.

Some or all of the bending required could be effected by hand, either by grasping opposite ends of the skeleton and bending the whole structure in one operation, or by separately bending the skeleton about each of the appropriate lines of reduced stiffness. However, a tool may be desirable for this purpose, and indeed it may be essential depending on the resistance of the component to bending. FIG. 15 shows a tool which may be used. This comprises a shaft 501, with a handle 502 at one end. At the other end there is a protrusion 503, which extends at right angles to the shaft and has a cross section which is of a size to engage in a connection aperture 400 of one of the components. At the same end of the shaft as the protrusion a plate 504 extends at right angles to the shaft in the opposition direction to the protrusion. In use, the protrusion 503 is engaged in an aperture 400 in the component, and the plate is forced against the component at the location of the axis about which it is desired that bending should take place, and a transverse force is applied to the handle 502, so as to cause that bending to occur.

Figure 14:
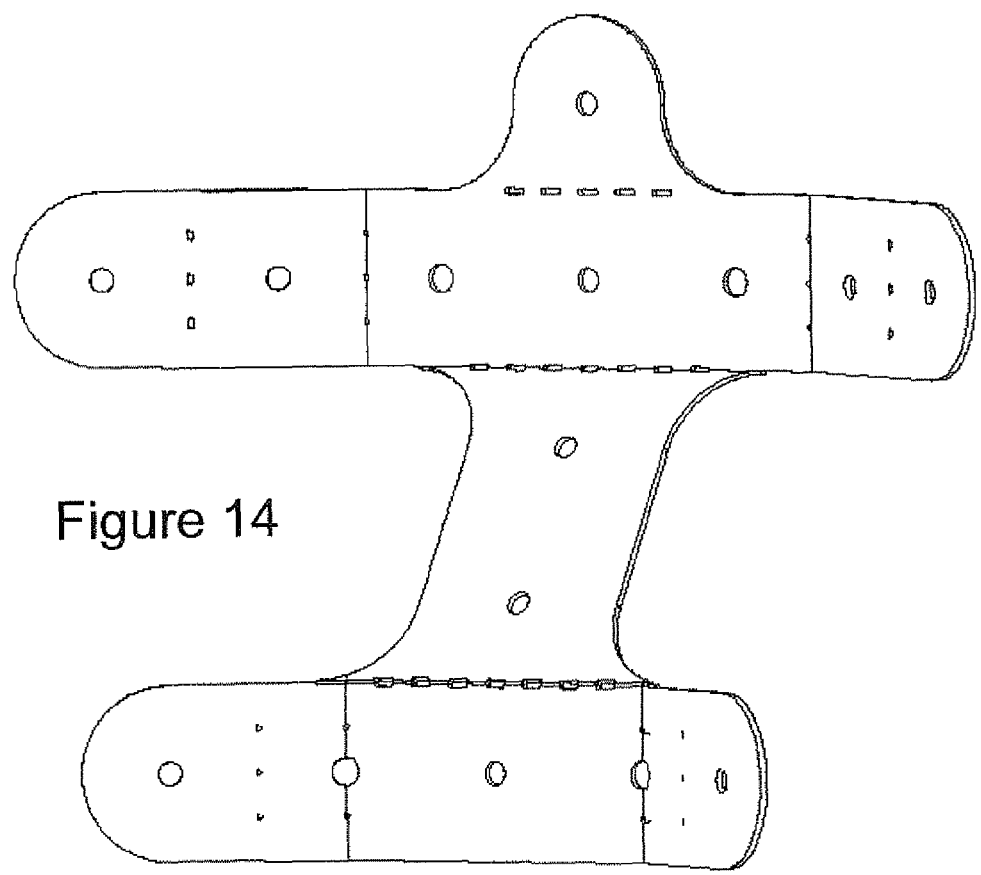
FIG. 14 shows an H-frame bent into a use position.

It is to be noted that although FIG. 14 shows the component as being constituted by a number of flat segments interconnected by sharp bends, i.e. with a radius of curvature which approaches zero, it would alternatively be possible for components to be formed with a more gradual curvature, i.e. with the radius of curvature being substantial. One way of doing this would be to use a tool having a forming surface with the appropriate radius of curvature, the relevant part of the component being forced against that forming surface. It is even possible that one more of the components might be curved throughout their length.

It is also to be noted that the different lines of reduced stiffness in a given component can be formed so as to permit bending with different degrees of ease, for example by altering the proportion of a given line which is removed to form the slots. This can be done either by altering the length of each slot or by altering the number of slots. In this way, when a bending force is applied to a component or combination of components, the three-dimensional shape produced by bending can be predetermined to a certain extent, with a view to making it easier to produce a support whose shape is generally suitable for use in relation to the anatomy generally to be found in potential wearers. Instead of forming the lines of reduced stiffness by means of slots, it is alternatively possible to form grooves extending along the desired lines, or a plurality of grooves arranged similarly to the plurality of illustrated slots to form each line. When grooves are used, one additional way of altering the ease of bending is to alter the depth of the grooves.

The illustrated components can be made in various ways, and of various materials. By way of example, however, the components can be laserjet cut, including the cutting to form the lines of weakness and the holes through which the bolts go to hold the components together, from 1.5 mm thick steel plate, for example painted mild or stainless steel. One alternative material to steel is a thermoplastic resin/carbon fiber composite, though this is believed to be less satisfactory than steel. As an alternative to laser cutting, the components can be formed by stamping.

To produce the final supports, the skeleton formed from one or more frame and one or more extension needs to be provided with sufficient padding to cushion the wearer's head and neck against localised high forces being applied by the skeleton, and to prevent the wearer's head being abraded by the skeleton. For this purpose the individual components of the skeleton are each preferably covered, as mentioned above, with padding, at least on the sides of the components which face towards the wearer. The padding preferably employs foam, which can be a visco-elastic foam or a non-viscoelastic foam. To enable a foam element to be attached to a component of the skeleton, the component can be wholly or partly covered on its front surface, i.e. the surface facing the wearer, with pieces of hook material, for example that sold under the Trade Mark Velcro, attached to the component, for example by gluing. In assembling the frame(s) and extension(s) to form a skeleton, each extension is attached to that surface of the frame which is remote from the wearer's head. This means that each frame can be wholly covered by padding, as it will always be wholly adjacent the wearer's head. However, the hook material can be omitted from those surfaces of extensions which never need to be padded, whatever form the skeleton may take.

The padding elements which are to be used are each provided on one of their surfaces with Velcro eye material, or the whole of each padding element is enveloped in a material, such as brushed nylon, which adheres well to a material such as Velcro eye material. Conveniently, the padding elements are in the form of circular pads. The padding elements can be made by punching the circular (or other shaped) pads out of a sheet of foam sandwiched between sheets of cover material. If the properties of the foam are selected carefully, the top and bottom cover material will stick to itself along the outer periphery of the pad, forming a continuous cover over the foam. To ensure that this smooth and soft edge does not delaminate, the punching tool preferably has a heating element around the periphery, which melts the edges (a form of heat welding) of the covering material. This gives a pad which has a reasonably long lasting seam and which can be cleaned in a mechanical washing machine, whilst being mass producible and hence of lower cost than would be the case if the cover material were sewn around the foam.

Alternatively, modular pads can be sewn from thin foam with Velcro hook material laminated to one side only. By suitably shaping this foam material, e.g. by CNC cutting (where CNC stands for computer numerically controlled), and folding it over during the stitching process the outer layer of the modular cover has, as with the pads described above, an outer surface which will adhere to the Velcro eye material that is already attached to the frames and parts of the extensions. An opening on one side of these modular covers, suitably closed with Velcro eye and hook or a zipper, will allow different density modular foam inserts to be used, including ones with visco-elastic properties.

Another possibility is to use non-circular modular pads which are oversize to the length and width of the frame plus extensions. By additionally applying hook material, e.g. Velcro hook material, to the outer surfaces of the frames and/or extensions, i.e. the surfaces which in use face away from the wearer, the oversize pads can be drawn over the edges of the frames and extensions, and attached to these outer surfaces. This has the result that the pads protect the wearer from the hard edges of the frame and extensions. The oversize modular pads can be made, for example, by either of the techniques described in the two preceding paragraphs, i.e. by punching and hot welding, or by sewing.

Yet another possibility is for some parts of the modular frames and extensions to be covered in pre-shaped, one piece covers, where stitching cuts through the foam during the edge sewing process.

The invention claimed is:

1. A kit of parts for forming an orthotic head and neck support, comprising at least one frame having a plurality of arms extending from a central region, at least one extension connectable to the at least one frame, and means for attaching the at least one extension to the at least one frame, wherein at least one of said at least one frame and said at least one extension is bendable to conform the support to the shape of at least one of a wearer's head and neck, the kit further comprising padding members connectable to at least one of the at least one frame and said at least one extension on the surface thereof which in use is to be adjacent the wearer, the kit further comprising a mounting bracket for attaching the orthotic head and neck support to a chair, a bed, or another structure in which the wearer may sit or lie.

2. A kit according to claim 1, wherein said at least one frame comprises at least one of:
   (a) A W-frame having three parallel vertical elements, with each adjacent pair of elements being interconnected by a cross element, and an element extending outwardly from the outermost of the three parallel elements;
   (b) A Y-frame having a vertical element with two further elements extending from the lower end of the vertical element in a direction angled downwardly;
   (c) An H-frame having two horizontal elements connected intermediate their ends by a vertical element.

3. A kit according to claim 2, wherein the Y-frame has each of the said downwardly angled elements connected to the vertical element by a horizontal element.

4. A kit of parts according to claim 2, wherein the H-frame has one of its horizontal elements longer than the other.

5. A kit of parts according to claim 2, wherein the H-frame has its horizontal elements connected by the vertical element midway between their ends.

6. A kit of parts according to claim 2, wherein said at least one extension comprises at least one of:
   (a) A straight extension;
   (b) An L-shaped extension;
   (c) An extension having two elements extending at an acute angle to one another.

7. A kit of parts according to claim 6, wherein the acute angle is 45°.

8. A kit of parts according to claim 2, comprising a plurality of connection members, wherein the at least one extension is connectable to one of said at least one frames by the connection members, the at least one extension being provided with apertures through which a connection member can be passed.

9. A kit of parts according to claim 8, wherein the connection members are screwthreaded.

10. A kit of parts according to claim 2, wherein said at least one frame and/or said at least one extension have at least one line of reduced stiffness formed therein, about which said frame or extension is preferentially bendable.

11. A kit of parts according to claim 10, wherein the or each line of reduced stiffness is formed by one or more slots or holes.

12. A kit of parts according to claim 10, wherein the or each line of reduced stiffness is formed by a groove.

13. A kit of parts according to claim 2, wherein said at least one frame and/or at least one extension has a plurality of lines of reduced stiffness formed therein, with the lines of reduced stiffness differing from one another in the ease with which bending about the lines is possible.

14. A kit of parts according to claim 2, wherein the or each frame has a hook material on the surface thereof which in use is adjacent the wearer, and the padding members have a loop material thereon which enables the padding members to be attached to the frame by inter-engagement of the hook members and loop members.

15. A kit of parts according to claim 14, in which the or each extension also has hook material on at least part of one surface thereof.

16. An orthotic head support formed from a kit of parts according to claim 2, by attachment of said at least one extension thereof to said at least one frame thereof.

17. A kit of parts according to claim 3, wherein said at least one extension comprises at least one of:
   (a) A straight extension;
   (b) An L-shaped extension;
   (c) An extension having two elements extending at an acute angle to one another.

18. A kit of parts according to claim 4, wherein said at least one extension comprises at least one of:
   (a) A straight extension;
   (b) An L-shaped extension;
   (c) An extension having two elements extending at an acute angle to one another.

19. A kit of parts according to claim 5, wherein said at least one extension comprises at least one of:
   (a) A straight extension;
   (b) An L-shaped extension;
   (c) An extension having two elements extending at an acute angle to one another.

20. An orthotic head support formed from a kit of parts according to claim 6, by attachment of said at least one extension thereof to said at least one frame thereof.

* * * * *